United States Patent [19]

Yon et al.

[11] Patent Number: 5,237,111

[45] Date of Patent: Aug. 17, 1993

[54] LIQUID ADSORPTION PROCESS TO PRODUCE AN ULTRA PURE PRODUCT

[75] Inventors: Carmen M. Yon, Carmel, N.Y.; John P. Brady, Algonquin, Ill.; Joe Quock, Hopewell Junction, N.Y.

[73] Assignee: UOP, Des Plaines, Ill.

[21] Appl. No.: 930,637

[22] Filed: Sep. 25, 1992

Related U.S. Application Data

[63] Continuation-in-part of Ser. No. 717,969, Jun. 20, 1991, abandoned.

[51] Int. Cl.$^5$ ..................... C07C 41/06; C07C 41/36
[52] U.S. Cl. ................................ 568/697; 568/699
[58] Field of Search ............................... 568/697, 699

[56] References Cited

U.S. PATENT DOCUMENTS

| | | | |
|---|---|---|---|
| 2,720,547 | 10/1955 | Wolff et al. | 260/614 |
| 4,118,425 | 10/1978 | Herbstman | 260/614 A |
| 4,219,678 | 8/1980 | Obenaus et al. | 568/697 |
| 4,329,516 | 5/1982 | Al-Muddarris | 568/697 |
| 4,465,870 | 8/1984 | Herskovits | 568/697 |
| 4,575,566 | 3/1986 | Vora | 568/697 |
| 4,734,199 | 3/1988 | Nagji et al. | 210/674 |
| 4,814,517 | 3/1989 | Trubac | 568/697 |
| 4,816,607 | 3/1989 | Vora et al. | 568/697 |

FOREIGN PATENT DOCUMENTS 0229994  7/1987  European Pat. Off. ............ 568/699

OTHER PUBLICATIONS

Chemical Engineering News, p. 35, Jun. 25, 1979.
Paper presented at The American Institute of Chemical Engineers, 85th National Meeting, Jun. 4-8, 1978.
Hydrocarbon Processing, p. 91, Oct., 1980.
Hydrocarbon Processing, vol. 54, No. 2, pp. 97-98, 1975.
Chemical Engineering, pp. 83-87 Jul. 9, 1973.

Primary Examiner—Marianne M. Cintins
Assistant Examiner—Michael B. Hydorn
Attorney, Agent, or Firm—Thomas K. McBride; John G. Tolomei; Richard P. Silverman

[57] ABSTRACT

A process for the etherification and separation of $C_3$–$C_5$ hydrocarbons is improved by the advantageous integration of an oxygenate recovery unit having a 3-bed arrangement into the etherification separation section. A feedstream including $C_3$ hydrocarbons and isobutene are reacted with methanol in an etherification to produce an etherification effluent that is separated in a first separator into a bottoms stream of MTBE product and an overhead stream of unreacted isobutane, methanol, other oxygenate compounds and $C_3$-hydrocarbons. After recovery of methanol, in an adsorptive separation process, the methanol deficient overhead stream enters a second separation zone in the form of depropanizer for the separation of isobutane and higher boiling hydrocarbons from the $C_3$ hydrocarbons. Any oxygenate compounds that are carried from the bottom of the column with the $C_4+$ hydrocarbon stream are removed in an oxygenate recovery unit designed to produce an ultra pure product essentially free of oxygenates. A portion of the purified hydrocarbons from the oxygenate recovery unit are recycled as regenerant through the oxygenate recovery unit to desorb oxygenate compounds. This integration of the oxygenate recovery unit provides a closed loop for its regeneration that utilizes existing separation facilities for the removal of oxygenate compounds from the hydrocarbons of the regenerant stream.

22 Claims, 2 Drawing Sheets

LIQUID ADSORPTION PROCESS TO PRODUCE AN ULTRA PURE PRODUCT

This application is a continuation-in-part of copending U.S. application Ser. No. 717,969, filed Jun. 20, 1991 now abandoned.

FIELD OF THE INVENTION

This invention relates broadly to adsorption processes. In more limited aspects this invention relates to processes for the production of ethers by the reaction of olefins with an alcohol. In yet more limited aspects this invention more directly relates to a process for the etherification of a dehydrogenation effluent and the recyle materials from the etherification zone to an isomerization zone and to the dehydrogenation zone wherein the unreacted etherification reaction product is recovered essentially free of oxygenated species prior to subsequent processing.

BACKGROUND OF THE INVENTION

Etherification processes are currently in great demand for making high octane compounds which are used as blending components in lead-free gasoline. These etherification processes will usually produce ethers by combination of an isoolefin with a monohydroxy alcohol. The etherification process can also be used as a means to produce pure isoolefins by cracking of the product ether. For instance, pure isobutylene can be obtained for the manufacture of polyisobutylenes and tert-butyl-phenol by cracking methyl tertiary butyl ether (MTBE). The production of MTBE has emerged as a predominant etherification process which uses $C_4$ isoolefins as the feedstock. A detailed description of processes, including catalyst, processing conditions, and product recovery, for the production of MTBE from isobutylene and methanol are provided in U.S. Pat. Nos. 2,720,547 and 4,219,678 and in an article at page 35 of the Jun. 25, 1979 edition of Chemical and Engineering News. The preferred process is described in a paper presented at The American Institute of Chemical Engineers, 85th National Meeting on Jun. 4-8, 1978, by F. Obenaus et al. Other etherification processes of current interest are the production of tertiary amyl ether (TAME) by reacting $C_5$ isoolefins with methanol, and the production of ethyl tertiary butyl ether (ETBE) by reacting $C_4$ isoolefins with ethanol.

Due to the limited availability of olefins for etherification, it has become common practice to produce them by the dehydrogenation of isoparaffins and to pass the dehydrogenation effluent to an etherification process. Processes for producing olefins by the dehydrogenation of saturated hydrocarbons are well known. A typical dehydrogenation process mixes the feed hydrocarbons with hydrogen and heats the resulting admixture by indirect heat exchange with the effluent from the dehydrogenation zone. Following heating, the feed mixture passes through a heater to further increase the temperature of the feed components before it enters the dehydrogenation zone where it is contacted with the dehydrogenation catalyst. The catalyst zone may be operated with a fixed bed, a fluidized bed, or a movable bed of catalyst particles. After heat exchange with the feed, the dehydrogenation zone effluent passes to product separation facilities. The product separation facilities will typically produce a gas stream, made up primarily of hydrogen, a first product stream that includes the desired olefin products, and a second potential product stream comprising light hydrocarbons. The light hydrocarbon stream typically has fewer carbon atoms per molecule than the desired olefin product. Light hydrocarbons are generally removed from the product stream in order to reduce flow volume, operating pressures, and undesirable side reactions in downstream process units that receive the olefin product. A portion of the hydrogen stream is typically recycled to the dehydrogenation zone to provide hydrogen for the combined feedstream. The product stream usually contains uncovered dehydrogenatable feed hydrocarbons in addition to the product olefin. These unconverted hydrocarbons may be withdrawn in separation facilities for recycle to the dehydrogenation zone or passed together with the product olefins to an etherification zone for conversion of the product olefins to ethers.

General representations of flow schemes where a dehydrogenation zone effluent passes to an etherification zone are shown in U.S. Pat. Nos. 4,118,425 and 4,465,870. More complete representations of a flow arrangement where the dehydrogenation zone effluent passes to an etherification zone are given in U.S. Pat. No. 4,329,516 and at page 91 of the October, 1980 edition of Hydrocarbon Processing. The latter two references depict the typical gas compression and separation steps that are used to remove hydrogen and light ends from the dehydrogenation zone effluent before it passes to the etherification zone. A typical effluent from an etherification zone includes an ether product, unreacted alcohol, and unreacted hydrocarbon and by-product ethers and alcohols. These effluent components enter separation facilities that yield the ether product, alcohol for recycling to the etherification zone, and hydrocarbons for further processing into dehydrogenation. This recycle stream of $C_4$ or $C_5$ isoparaffins, prior to recycling to the isomerization zone and the dehydrogenation zone, is usually treated to recover methanol and remove other oxygenates which are harmful to the isomerization and the dehydrogenation catalysts.

In the application where isomerization is used to produce more isoparaffin feed to the dehydrogenation unit U.S. Pat. No. 4,816,607, the recycle stream following the removal of oxygenates is combined with hydrogen and passed to a complete saturation process wherein any olefin and diolefins are saturated. The saturated stream is introduced to a fractionation zone along with additional $C_4$ saturates. A side draw stream comprising normal $C_4$ hydrocarbons is removed from the fractionation zone and passed over a catalyst in an isomerization reactor to convert the normal hydrocarbons to isoparaffins. The reactor effluent comprising isoparaffins is returned to the fractionation zone and a concentrated stream of isoparaffins is withdrawn from the top of the fraction zone and returned to the dehydrogenation zone.

The oxygenate compounds in the etherification zone effluent create problems such as catalyst deactivation or fouling in downstream processes that receive these unreacted hydrocarbons. For example where the unreacted hydrocarbons are recycled to a dehydrogenation zone, MTBE and tertiary butyl alcohol (TBA) may be present in the recycle stream. Oxygenate compounds present in the recycle stream can include etherification reactants such as alcohols. In particular the incomplete recovery of methanol from the etherification zone exacerbates the problem by increasing the oxygenate concentration in the recycle stream.

Oxygenates are often removed by adsorption processes. In typical operation of an adsorptive oxygenate removal unit the system uses two beds or multiples of two beds wherein one bed is operating in the adsorption mode and the other is operating in the regeneration mode.

In the adsorption art, 3-bed systems typically are used when the mass transfer zone for a particular separation is longer than one bed. The 3-bed configuration has two beds in series during the adsorption mode to allow the mass transfer zone to spill over from the lead bed into the second or trim bed in order to more completely load the lead bed to its equilibrium capacity. At the point of breakthrough from the trim bed, the unused adsorbent capacity remaining in the lead bed has normally reached less than 25% unused capacity. In a typical application for natural gas sweetening plants and natural gas dehydrators which exhibit long mass transfer zones, this lead/trim series configuration can add from 5-10% to the capacity of a single bed. A detailed discussion of adsorption systems including 3-bed configurations is described in an article at page 98 appearing in Hydrocarbon Processing, Volume 54, No. 2 and at page 86 appearing in Chemical Engineering, Jul. 9, 1973. In the adsorption of oxygenates from a light hydrocarbon mixture of iso and normal alkanes and alkenes, the mass transfer zone is relatively short and typically carried out in a single bed or part of a single bed (U.S. Pat. No. 4,814,517). Even though a 3-bed system is disclosed in U.S. Pat. No. 4,734,199 for a liquid phase process for the removal of methanol, each bed operates independently in the adsorption mode, although the beds are coupled during a liquid phase regeneration to provide conservation of the regenerant fluid.

Processes are sought which continuously produce an ultra pure product stream of unreacted hydrocarbons which are essentially-free of oxygenates. Although single bed systems have been proposed as described hereinabove, these single bed systems are not resilient to sudden variations in feed composition such as a spike of oxygenates resulting from an upset in upstream processing. In addition, a residual amount of spent regenerant remaining in an adsorbent bed following regeneration is often sufficient to contaminate the ultra pure product.

BRIEF SUMMARY OF THE INVENTION

It is a broad object of this invention to provide an effective means for removing oxygenate compounds to produce an ultra pure stream of unreacted hydrocarbons. The present invention employs a lead/trim configuration with three beds or multiples of three beds wherein each bed moves cyclically from the trim mode, to the lead mode and then to the regeneration mode. The function of the trim mode is to provide additional adsorption media to provide a guard bed to achieve the ultra pure product regenerant in the event of upsets, to provide a greater utilization of the lead bed adsorbent, and to minimize the potential for product contamination during the displacement steps while switching between lead/trim bed positions during the cycle. A critical aspect of the invention is the finding that the retention of sufficient capacity in the trim bed at the end of the adsorption step will permit the production of the ultra pure product during the switching of the bed from trim to lead position.

In the case of the instant invention where there is a requirement for an ultra pure product containing between 1 and 0.1 ppm weight of oxygenates, the trim bed functions as a guard bed providing a significant safety margin against plant upsets, and further providing incremental capacity to continue producing ultra pure product during the switching of beds from the trim to the lead position. The 3-bed cycle provides a more complete capacity utilization of the lead bed, which at the end of the trim mode in the cycle has reached less than 10% unused capacity, while the trim bed still has 90% of its capacity unused. At the end of the adsorption cycle in the lead bed, the detectable concentration of 1 ppm has proceeded less than half the distance through the trim bed. Thus, even at a point late in the adsorption cycle, the two beds could tolerate a sudden and significant transient surge of concentration without experiencing breakthrough to contaminate the ultra pure product. One would not normally consider this cost of equipment and adsorbent justified for a 10% increase in capacity alone.

In a preferred embodiment of the process of the present invention, oxygenates comprising light alcohols and ethers are adsorbed from a liquid hydrocarbon feedstock in the liquid phase to produce an ultra pure product. A liquid hydrocarbon feedstock is passed to a first of two adsorbent beds simultaneously operating in a lead/trim configuration at adsorption conditions. Each of the adsorbent beds have a feed end and an effluent end, and each of the adsorbent beds contain a solid adsorbent. The solid adsorbent has a useful capacity and a selectivity for the adsorption of the oxygenates. A mass transfer zone is established in the first adsorption bed, and an intermediate stream is withdrawn from the effluent end of the first adsorbent bed. The intermediate stream is passed to the feed end of a second adsorbent bed and an ultra pure product with an oxygenate concentration of less than 1 ppm weight is withdrawn from the second adsorbent bed. The above steps are continued until the mass transfer zone has proceeded through the first adsorbent bed and is established in the second adsorbent bed at a point where the mass transfer zone has used less than about 10% of the useful capacity of the second adsorbent bed. At this point, the passage of the hydrocarbon feedstock to the first adsorbent bed is terminated and the hydrocarbon feedstock is passed to a third adsorbent bed. The third adsorbent bed has undergone regeneration and contains a liquid regenerant in the void spaces of the solid adsorbent. As the hydrocarbon feedstock is passed to the third bed, it displaces the liquid regenerant from the third adsorbent bed to provide a displaced liquid regenerant. The displaced liquid regenerant is passed to the first adsorbent bed, and an unadsorbed feedstock stream from the first adsorbent bed is passed to the second adsorbent bed. The ultra pure product is recovered from the second adsorbent bed for the duration of the displacement. The passage of hydrocarbon feedstock to the third adsorbent bed is terminated and the hydrocarbon feedstock is passed to the second adsorbent bed to provide the intermediate stream. The intermediate stream from the second adsorbent bed is passed to the third adsorbent bed and the ultra pure product is recovered from the third adsorbent bed. The flow of displaced liquid regenerant to the first adsorbent bed is terminated and the first adsorbent bed is isolated. The displaced liquid regenerant is drained from the first adsorbent bed, and a superheated regenerant vapor is passed to the first adsorbent bed at a temperature effective to desorb oxygenates from the solid adsorbent and recover the oxygenates from the first adsorbent bed in a spent regenerant vapor stream.

The first adsorbent is cooled by passing liquid regenerant to the feed end of the first adsorbent bed and the liquid regenerant is recovered. The flow of liquid regenerant to the first adsorbent bed is terminated, and periodically, the process cycle is incremented for the second and third adsorbent beds.

Another object of this invention is to provide a method of producing an ultra pure stream of unconverted hydrocarbons from an etherification zone effluent. In a limited aspect a relatively simple and effective arrangement for separating the effluent from an etherification zone and providing an isoalkane effluent stream that is essentially free of oxygenate compounds has been discovered. Thus, in a broad aspect this invention charges a feedstream containing saturated and unsaturated $C_4$-$C_5$ hydrocarbons to an etherification zone. The etherification feedstream includes isoolefins and $C_3$ hydrocarbons wherein the isoolefins are reacted with a monohydroxy alcohol to produce an ether product in an etherification zone effluent that is deficient in the reacted isoolefin. The etherification effluent is separated to recover the ether product and the portion of the etherification zone effluent containing unreacted hydrocarbons is passed through a methanol recovery zone for the recovery of methanol and a fractionation zone to remove $C_3$ and lighter hydrocarbons from the stream of unreacted $C_4$-$C_5$ hydrocarbons. Lighter oxygenate compounds are removed by the fractionation of the $C_3$ hydrocarbons. The unreacted $C_4$-$C_5$ hydrocarbons and the remaining heavier oxygenate compounds is hereinafter referred to as feedstock. Heavier oxygenate compounds are removed by passing this feedstock of unreacted hydrocarbons through a separate oxygenate recovery unit.

In a typical etherification separation as much as 100 wt. ppm heavy oxygenate compounds can be carried over with the unreacted hydrocarbon stream and appear in the feedstock. By the method of this invention, the concentration of such heavy oxygenate compounds in the unreacted hydrocarbon stream is typically reduced to a range of 10 to 1 ppm wt. and more preferably a range of 1 to 0.1 ppm wt. Such low levels of oxygenate compounds allow the unreacted hydrocarbon stream to be used as a feed in a variety of processes. One such process is the butane isomerization of the stream into additional feedstock for the dehydrogenation zone. It is also possible to use this stream as part of the feed to an alkylation reaction zone to produce high octane alkylate that can be used in combination with the MTBE product.

In a more limited embodiment, this invention is a process for producing ethers. An etherification feedstream comprising isoolefins and isoalkanes having 4 or 5 carbon atoms is passed to an etherification zone. The etherification feedstream is combined with a $C_1$-$C_5$ monohydroxy alcohol in the etherification zone. The etherification zone is maintained at etherification conditions to obtain essentially complete conversion of the etherification feedstream and to provide an etherification zone effluent comprising isoalkanes, alcohol, ethers and light hydrocarbons. The etherification zone effluent is passed to a first separation zone. At least a first stream comprising an ether product and a second stream comprising isoalkanes, light hydrocarbons and oxygenate compounds, including alcohol and ethers is recovered. At least a portion of the alcohol from the second stream is recovered in an alcohol recovery zone to provide a recovered alcohol. At least a portion of the recovered alcohol is returned to the etherification zone. The remainder of the second stream from the alcohol recovery zone is passed to a second separation zone to separate isoalkanes from the second stream and obtain a third stream comprising isoalkanes and oxygenates. The third stream is passed to an adsorption zone that uses separate adsorbent beds containing a solid adsorbent having void spaces. The solid adsorbent has a useful capacity and a selectivity for the adsorption of oxygenates. Two of the separate adsorption beds are operated simultaneously in a lead/trim configuration at adsorption conditions. Each of the adsorbent beds has a feed end and an effluent end. The oxygenates are adsorbed in the adsorption zone by passing the third stream to a first of two adsorbent beds to establish a mass transfer zone in the first adsorbent bed. An intermediate stream is withdrawn from the effluent end of the first adsorbent bed and passed to the feed end of a second adsorbent bed. An ultra pure product having an oxygenate concentration of less than 1 ppm wt. is withdrawn from the second adsorbent bed. The above adsorption step is continued until the mass transfer zone has proceeded through the first adsorbent bed and is established in the second adsorbent bed at a point where the mass transfer zone has used less than 10% of the useful capacity of the second adsorbent bed. The passage of the third stream to the first adsorbent bed is terminated. The third stream is passed to a third adsorbent bed that has undergone regeneration and contains a liquid regenerant in the void spaces of the solid adsorbent. The liquid regenerant from the third adsorbent bed is displaced by passing the third stream therethrough to provide a displaced liquid regenerant stream. The displaced liquid regenerant is passed to the first adsorbent bed. An unadsorbed feedstock stream is passed from the first adsorbent bed to the second adsorbent bed and the ultra pure product is recovered from the second adsorbent bed for the duration of the displacement step. The passage of the third stream to the third adsorbent bed is terminated and the third stream is passed to the second adsorbent bed. The intermediate stream is recovered from the second adsorbent bed. The intermediate stream is passed to the third bed and the ultra pure product is recovered from the third adsorbent bed. The flow of the displaced liquid regenerant to the first adsorbent bed is terminated and the first adsorbent bed is isolated. The displaced liquid regenerant is drained from the first adsorbent bed and a superheated regenerant vapor stream is passed to the first adsorbent bed at a temperature effective to desorb oxygenates from the solid adsorbent. The oxygenates are recovered from the first adsorbent bed in a spent regenerant vapor stream. The first adsorbent bed is cooled by passing a liquid regenerant to the feed end of the first adsorbent bed and recovering the liquid regenerant. The flow of liquid regenerant to the first adsorbent bed is terminated and the process cycle for the adsorption and regeneration steps is periodically incremented for the second and third adsorbent beds. The ultra pure product is passed from the adsorption zone into the first separation zone.

Additional embodiments, aspects and details of this invention are set forth in the following detailed description.

DETAILED DESCRIPTION OF THE INVENTION

The adsorption process of this invention produces an ultra pure product by the removal of oxygenates in an oxygenate removal unit (ORU) from a liquid hydrocarbon feedstock. The term ultra pure product in this description refers to a $C_4$ or $C_5$ hydrocarbon stream which contains less than 1 ppm wt. and preferably between 1 ppm wt. and 0.1 ppm wt. oxygenates. The process comprises passing the ORU feedstock to a first of 3 adsorbent beds or groups of 3-adsorbent beds wherein each bed contains a solid adsorbent having selectivity of the adsorption of trace amounts of oxygenates. The first and second adsorbent beds are operated in a lead/trim configuration wherein the liquid hydrocarbon feedstock enters the lead or first adsorbent bed, the effluent of the first adsorbent bed flows to the feed end of the trim or second adsorbent bed, and an ultra pure product essentially free of oxygenates is withdrawn from the second adsorbent bed.

The lead adsorbent bed and the trim adsorbent bed each have a useful capacity, or breakthrough capacity. The useful capacity is a measure of the total amount of adsorbable material taken up by an adsorbent bed at the point where the adsorbable material begins to appear in the effluent. The adsorbent equilibrium capacity is the point when the adsorbent is fully saturated with the adsorbable material. Typically, the adsorption process cycle is stopped before the adsorbent is fully saturated. The portion of the bed that is not saturated to an equilibrium level is called the mass transfer zone. The parameters affecting the size and shape of a mass transfer zone are adsorbent type, adsorbent equilibrium capacity, flow rate, packed-bed depth, adsorbent particle size, physical properties of the carrier fluid, temperature, pressure, and the concentration of adsorbable material in the carrier fluid. If conditions are chosen that are favorable to mass transfer (e.g., long contact time), then the mass transfer zone is small when compared to the total amount of adsorbent bed employed. In such conditions, adsorbent bed utilization is more efficient and the breakthrough (or useful) capacity closely approaches the true equilibrium capacity. More often, conditions cannot be optimized based on the adsorbent needs but are fixed by the overall process needs. This may dictate unfavorable mass-transfer conditions when practical packed-bed diameters and depths must be employed. Actual adsorbent bed utilization is then less efficient and the breakthrough capacity falls short of the equilibrium capacity.

In the instant invention, wherein two adsorbent beds are employed in a lead/trim configuration, the mass transfer zone moves from the inlet end of the lead bed, travels through the lead bed, and enters the trim bed. The passage of the mass transfer zone in the trim bed is terminated at a point where the remaining capacity within the trim bed is sufficient to provide an ultra pure product from an unadsorbed feedstream during the displacement period. Preferably, the passage of the mass transfer zone in the trim bed is terminated at a point where the mass transfer zone has used less than about 10% of the useful capacity of the trim bed and there is greater than about 90% useful capacity remaining in the trim bed.

In the process cycle of this invention, the passage of the feedstock into the first adsorbent bed is terminated and the feedstock is passed to a third bed which was recently regenerated and contains a liquid regenerant in the void volume spaces of the solid adsorbent. In a displacement step, ORU feed is introduced to the third bed and the regenerant in the third bed is transferred from the third bed to the first bed which is in the lead position. At the same time the contents of the first bed comprising unadsorbed feedstock, are displaced to the second bed, in the trim position, and a final ultra pure product is withdrawn from the second bed. At the end of the displacement step, the first bed, now filled with liquid regenerant is isolated, and the second bed is moved to the lead position by the introduction of fresh feedstock to the second bed and the flow of ORU feed to the third bed is terminated. The effluent of the second bed is sent to the third bed, placing it in the trim position, and the ultra pure product is withdrawn from the third bed.

The oxygenate recovery unit of this invention uses adsorptive separation to retain the heavier oxygenate compounds. More particularly, the oxygenate recovery unit of this invention is a continuous process for the liquid phase adsorption of oxygenate compounds combined with the cyclic regeneration of the adsorbent media with a vapor phase regenerant stream of $C_3$-$C_6$ hydrocarbons. Specifically, this invention is a process using a multiple bed adsorbent zone, preferably having three beds, wherein at least two of the beds are arranged in series comprising a lead bed and a trim bed, and at least one other bed is being regenerated. The feedstock is fed to the lead bed and oxygenate-free product is withdrawn from the trim bed. The operation of the process takes place in the following sequence when considering the operation of a single adsorber bed. At the beginning of the cycle in the trim mode (T), the oxygenate-free product is withdrawn from the bed in the trim position and it receives feed from another bed in the lead position. The system then enters a first displacement (D1) mode wherein product flow from the bed in the trim position continues as the remaining unadsorbed feedstock flows from the lead bed. At the conclusion of the D1 step, the trim bed is placed in the lead mode (L), wherein feedstock is charged to the lead bed and the effluent from the lead bed is charged to a newly regenerated bed now in the trim position. At the conclusion of the lead mode, a second displacement (D2) takes place wherein the bed continues to provide feed to a bed in the trim position, but the feed to the bed in the lead position is regenerant liquid which displaces the remaining unadsorbed feedstock from the lead bed to another bed in the trim mode. The former lead bed then enters a regeneration mode (R) comprising draining of the regenerant liquid; introducing regenerant vapor to heat the bed and to desorb the oxygenates; and cooling of the bed by introducing liquid regenerant to the feed end of the bed. At the completion of the regeneration cycle, the bed enters the third displacement step (D3) wherein the regenerant liquid is displaced from the regenerated bed to another bed now in the lead mode by introduction of feedstock. At the completion of the regeneration cycle, the regenerated bed is returned to the trim mode.

The first bed begins the regeneration procedure with the draining of the liquid regenerant from the first bed. A small amount of superheated vapor is provided at the top of the first bed to force the liquid regenerant from the bed and recover the regenerant in a separator. When the bed is completely drained, the heating step begins and the full flow of superheated regenerant is passed through the first bed from the top to desorb the oxygenates from the adsorbent. The spent regenerant vapor is condensed and recovered in a separator. A portion of the heat required to vaporize the regenerant is recovered by a heat recovery means. In the separator, the spent regenerant is separated to provide a hydrocarbon phase comprising regenerant and oxygenates and an aqueous phase comprising oxygenates. The hydrocarbon phase is recovered and returned to the separation zone in the etherification section. The aqueous phase is recovered and returned to the separation zone in the methanol removal section of the ether production complex.

At the conclusion of the heating step, the first bed is cooled and filled with liquid regenerant by passing liquid regenerant to the bottom of the first adsorbent bed and recovering the regenerant in the separator. At the end of the cooling and fill step the flow of regenerant to the first adsorption bed is stopped and the above cycles are begun on the next lead bed.

The above process is most suitable for the removal of trace oxygenates from the effluent of an etherification reaction after the following process steps: the separation of the ether product; the removal of the unreacted alcohol; the removal of $C_3$-minus hydrocarbons in a separation zone.

There are two feed materials to the subject process. One of the feed materials is a water-soluble alcohol which preferably has less than 4 carbon atoms per molecule. Thus, the alcohol can be chosen from methanol, ethanol, primary and secondary propanol, the various butanols, and other alcohols. However, the preferred class of alcohols are $C_4$-minus aliphatic monocyclic alcohols with methanol and then ethanol being particularly prefered. The majority of the description of the invention is presented in terms of the reaction of isobutene with methanol since these are the preferred feed materials and this is the commercially predominant reaction. However, it is not intended to thereby lessen the scope of the inventive concept. This is especially true since there have been predictions that the expected large demand for ethers as anti-knock additives will lead to the use of large amounts of ethanol produced by fermentation in the etherification processes.

The second feed materials is a $C_4$–$C_6$ acyclic hydrocarbon or a single carbon number mixture of isomeric hydrocarbons. The hydrocarbon feed material may therefore be substantially pure normal butane, normal pentane, or a mixture of the corresponding isomeric and normal hydrocarbons. The preferred hydrocarbon feedstream is a mixture of isobutane and normal butane such as is available from several sources in a petroleum refinery or as is available as field butanes. This variety of possible feed materials allows the production of a wide variety of ethers other than the preferred MTBE including methyl tertiary amyl ether, ethyl tertiary amyl ether, and ethyl tertiary butyl ether.

In a more limited embodiment, this invention is a process for producing MTBE that has an oxygenate removal unit for recovering an essentially oxygenate free recycle stream that is recycled to an isomerization zone and a dehydrogenation zone. In the process a recycle stream and a feedstream are combined to provide a dehydrogenation zone input stream. The feedstream comprises isobutane and hydrogen. The input stream is contacted with a dehydrogenation catalyst at dehydrogenation conditions in a dehydrogenation zone to obtain a first effluent stream comprising isobutene, isobutane, hydrogen and hydrocarbons having less than 4 carbon atoms. At least a portion of the first effluent stream is passed into a hydrogen recovery section to remove hydrogen from the first effluent. The first effluent from the hydrogen recovery section is passed to an etherification zone where it is combined with methanol and contacted in an etherification zone with an etherification catalyst at etherification conditions to react essentially all of the isobutene and obtain a second effluent stream comprising isobutane, MTBE, methanol, dimethylether, tertiary butyl alcohol, TBA, other oxygenate compounds, water and hydrocarbons having less than 4 carbon atoms. The second effluent is separated in a first separation zone in the etherification zone to produce an MTBE product stream containing a majority of the TBA and a separator stream that comprises isobutane, methanol, DME, TBA and water and other oxygenates, and includes hydrocarbons having less than 4 carbon atoms. The separator stream is passed to a methanol recovery zone that recovers a majority of the methanol from the separator stream. At least a portion of the methanol from the methanol recovery zone is returned to the etherification zone. The remainder of the separator stream is passed to a second separation zone in the methanol recovery zone and separated into an overhead stream comprising $C_3$ hydrocarbons and lower boiling compounds comprising DME and water and a bottoms stream comprising oxygenate compounds. The bottoms stream is passed to an oxygenate removal zone comprising a 3-bed adsorption system and contacted therein with an adsorbent that selectively absorbs the oxygenate compounds and produces a recycle stream that is ultra pure and is essentially free of oxygenate compounds. Two beds of the 3-bed adsorption system operate in series while the third bed periodically is regenerated by passing at least a portion of a saturated recycle stream to the oxygenate recovery zone as a regenerant stream to desorb oxygenate compounds from the oxygenate recovery zone. The desorption stream is passed to the first separation zone for recovery of oxygenate compounds. The recycle stream is combined with hydrogen and passed to a complete saturation unit which catalytically saturates any remaining olefins and diolefins in the recycle stream to produce a saturated recycle stream. The saturated recycle stream is passed to a deisobutanizer column, wherein a stream of mixed butanes containing iso and normal butanes is introduced as feed, and a $C_5+$ stream is withdrawn from the bottom of the deisobutanizer column. At least a portion of the normal butane in the column is withdrawn as a side draw from the deisobutanizer and passed to a dryer to provide a dry normal butane feed for the isomerization reactor. The effluent from the isomerization reactor is returned to the deisobutanizer at a point in the deisobutanizer above where the normal butane side draw was made. Isobutane is withdrawn from the top of the deisobutanizer and recycled to the dehydrogenation zone.

Figure 1:
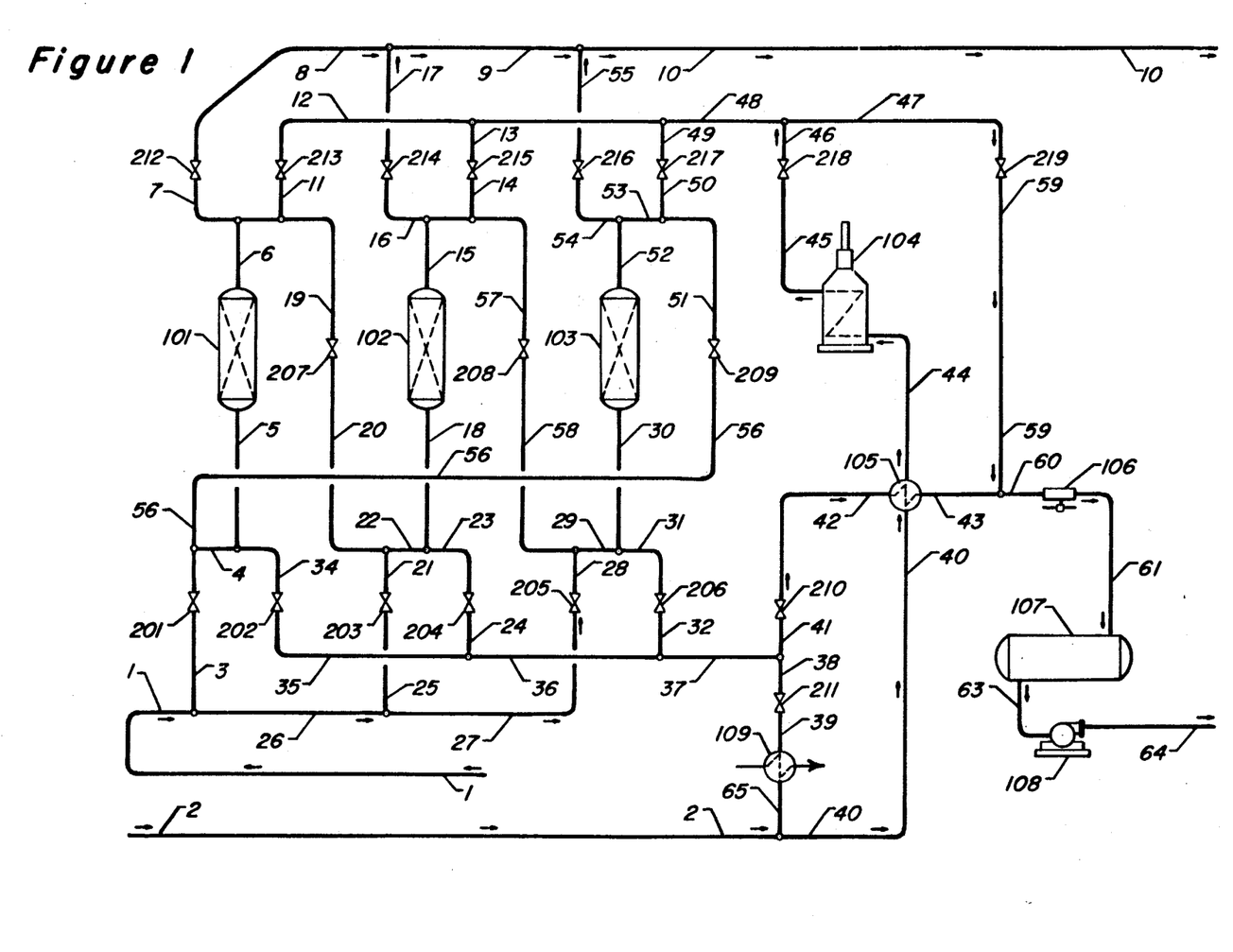
FIG. 1 is a schematic illustration of oxygenate removal process arrangement using 3-beds to produce an ultra pure product.

The invention is illustrated by the following process description mode with reference to the flow diagram of FIG. 1 of the drawings. The feedstock being treated in this illustrative process is the unreacted effluent from an MTBE unit which has undergone three separations to remove MTBE, to recover methanol and to remove light C$_3$-components. The etherification effluent is obtained by the catalyzed reaction of isobutylene with a stoichiometric excess of methanol in the liquid phase at a temperature of about 65 to about 90° C. The isobutylene reactant is introduced into the reactor as a mixture of trans butene, butadiene, isobutane and n-butane. The isobutylene constitutes about 45 mol. % of the C$_4$ hydrocarbon mixture, and is the only C$_4$ species which reacts with the methanol under the present conditions. The molar ratio of methanol to isobutylene is from about 1.05:1 to 1.5:1. The effluent from the reactor comprises product MTBE, unreacted methanol, unreacted C$_4$'s and small to trace amounts of dimethylether. TBA and other reaction by-products. This effluent is passed to a distillation unit wherein the MTBE product is recovered from the bottom. The overhead effluent from the distillation unit is typically water washed or passed to a separate adsorber unit to recover the bulk of the unreacted methanol from the etherification reaction and return the methanol to the etherification reaction zone. The resulting raffinate has the following typical amounts of oxygenates:

|  |  |
|---|---|
| Dimethylether | 50 ppm |
| Water | 50 ppm |
| Methanol | 5 ppm |
| TBA | 50 ppm |
| MTBE | 10 ppm | and is hereinafter referred to as the ORU feedstock. In the operation of this illustrative process, the overall cycle time requires 4320 minutes, i.e., the time interval from the beginning of an adsorption-purification step in one of the adsorption bed until the beginning of the next adsorption-purification step in the same bed.

With respect to FIG. 1, the liquid hydrocarbon feedstock enters the system through line 1. In a typical cycle, the liquid hydrocarbon feedstock first enters an adsorber bed 101 through lines 3, 4 and 5 at a rate controlled by valve 201. Adsorber bed 101 contains a zeolitic molecular sieve adsorbent having the capacity to adsorb trace quantities of oxygenates comprising methanol, MTBE, tertiary butyl alcohol (TBA), dimethylether, and water. Oxygenate selective adsorbents are used for the removal of these oxygenates from the hydrocarbons. A wide variety of adsorbents including activated alumina, silica gel and zeolite molecular sieves have been proposed for this class of separation. Zeolite adsorbents particularly zeolite 5A, zeolite 13X and zeolite D are preferred. It has also been taught in U.S. Pat. No. 4,814,517, the teachings which are hereby incorporated by reference, that a combination of silica gel and zeolite 13X in an adsorbent bed will provide superior adsorption of oxygenate compounds. A most preferred adsorbent for this purpose is the commercial zeolite widely known as zeolite 13X.

The temperature within adsorbent bed 101 is 26°-38° C. and pressure of 150 psig. Immediately prior to the introduction of the feedstock to adsorber bed 101, the bed was operating in the trim position, accepting feedstock from the lead bed and producing an ultra pure product. Before the feedstock entered the adsorber bed 101, all the beds in the system underwent a hereinafter described displacement step.

Feed passes through the bed 101 and the effluent from bed 101 is carried via lines 6 and 19 to valve 207 and from valve 207 through lines 20, 22 and 18 to adsorber bed 102 which is operating in the trim position. The ultra pure product essentially free of oxygenates is removed from adsorber bed 102 via lines 15 and 16, through valve 214, and lines 17, 9 and 10. Thus, adsorber beds 101 and 102 are initially operating in series in a lead/trim configuration. At the same time adsorbent bed 103 is in the regeneration mode. At the end of the lead period for adsorbent 101, the beds in the system undergo a displacement step. After the displacement step, adsorbent bed 102 shifts from the trim position to the lead position, adsorbent bed 101 formerly operating in the lead position will move to the regeneration position, and adsorbent bed 103 will move into the trim position. Just prior to the displacement step adsorbent bed 103, at the end of its regeneration cycle, contains a liquid regenerant, adsorbent bed 101 contains unadsorbed feedstock in the void spaces of the solid adsorbent, and adsorber bed 102 contains a portion of unadsorbed feedstock. As the displacement step begins, fresh feedstock is introduced to bed 103 via lines 1, 26, and 27, through valve 205 and through lines 28, 29 and 30. The regenerant fluid, initially in bed 103, is passed through lines 52, 53, 51, through valve 209 and lines 56, 4 and 5 to adsorbent bed 101. This step transferring the regenerant fluid to the lead bed prepares it for the regeneration cycle. Adsorbent bed 101 containing unadsorbed feedstock in the void spaces of the adsorbent, now passes this unadsorbed feedstock to the former trim bed, adsorbent bed 102, via lines 6, 19, valve 207, and lines 20, 22 and 18. Throughout the displacement step, ultra pure product is withdrawn from adsorbent bed 102 via lines 15 and 16, through valve 214 and on to lines 17, 9 and 10. Because adsorbent bed 102 had only a small amount of its useful or breakthrough capacity utilized, there is sufficient useful or breakthrough capacity remaining within the adsorbent bed in the trim position to continue to produce ultra pure product from the unadsorbed feedstock displaced from the lead adsorbent bed during this displacement step. At this point in the cycle, the mass transfer zone has used less than about 10% of the useful capacity of the adsorbent bed 102 and there is greater than about 90% of the useful capacity remaining in adsorbent bed 102. At the end of the displacement step, adsorbent 101 is isolated in preparation for the regeneration step, and feedstock flows through adsorbers 102 and 103. The ultra pure product is withdrawn from adsorbent 103 now in the trim position via lines 52 and 54, through valve 216 and on to lines 55 and 10. Valve 214 is closed at the end of the displacement step, and the effluent of adsorber bed 102 now in the lead position flows via lines 15, 57, valve 208, lines 58, 29 and 30 into adsorber bed 103. Valve 205 is closed and feed flows via lines 1, 26 and 25 to valve 203, lines 21 and 22 and 18 to enter bed 102.

Turning now to adsorber bed 101 which was isolated at the end of the displacement step. In accordance with this invention, oxygenate compounds are periodically desorbed from the adsorbent using a hydrocarbon regenerant stream. The regenerant stream comprises hydrocarbons having at least four carbon atoms and an oxygenate concentration of 1 to 0.1 wt. ppm. Sources of this regenerant stream include the purified hydrocarbon stream from the oxygenate recovery unit and C$_4$+hydrocarbon feedstreams. A portion of the purified hydrocarbon stream from the oxygenate removal zone is a preferred regenerant stream since it is deficient in unsaturated hydrocarbons. In order to further reduce the presence of unsaturates the regenerant stream is more preferably taken as an effluent from a hydrogenation unit. Adsorbent bed 101 will be regenerated in the vapor phase through the following three steps: pressure assisted drain, heating, and cooling. A small portion up to 20% of regenerant from line 2 is passed through line 40, through exchanger 105 and along line 44 to superheater 104. In superheater 104, the small portion of liquid regenerant is superheated to a temperature above 240° C. and the vapor is passed along line 45 through valve 218 and along lines 46, 48, and 12 to valve 213. From valve 213 the small amount of vapor passes through lines 11 and 6 and forces the regenerant liquid out of adsorbent bed 101 through lines 5 and 34, through valve 202 and along lines 35, 36 and 37 before it joins the remainder of the regenerant at line 41 and travels through valve 210 to line 42, through cross-exchanger 105 and on to line 43, past condenser 106 and is collected in separator 107 via line 61. When adsorbent 102 is at this point in the cycle, the liquid regenerant flows through lines 18, 23 and 24 controlled by valve 204 before joining line 36. Similarly, when adsorbent bed 103 is at this point in the cycle, the liquid regenerant flows through lines 30, 31 and 32 controlled by valve 206, before joining line 37. When the heating cycle is complete, adsorbent bed 102 begins a cooling cycle, wherein liquid regenerant is now brought in from line 2 through line 39, through valve 211 and lines 38, 37, 36 and 35. After all the regenerant has been drained from adsorbent bed 101, the full flow of regenerant is passed from line 2 through line 40 and exchanger 105 and through line 44 to superheater 104 where all the regenerant is now heated to a temperature in the range of 200°–300° C. The superheated vapor then travels via line 45, valve 218, lines 46, 48 and 12, reaching valve 213 and on through lines 11 and 6 to reach adsorbent bed 101. The heated vapor passes through adsorbent bed 101, desorbing the previously adsorbed oxygenates and removing them via lines 5 and 34 to valve 202, through lines 35, 36, 37, 41, past valve 210 to line 42 and through cross-exchanger 105. As the flow of vapor through adsorbent bed 101 continues, there is the potential to recover some of the heat of vaporization through cross-exchanger 105 as the cycle of heating continues. From cross-exchanger 105, the vapor travels to line 43 and condenser 106 where the material is condensed and transferred along line 61 to tank 107.

In producing an ultra pure product, it is important not to recycle any portion of the spent regenerant within the system during the regeneration process. Therefore, this spent regenerant, or desorption stream, is passed to another portion of the etherification complex such as the first separation zone wherein the recovery of the concentrated oxygenate compounds is possible. Spent regenerant leaves the oxygenate recovery unit from tank 107 via line 63 to pump 108 and is transferred from the unit via line 64.

When the heating cycle is complete, adsorbent bed 101 begins a cooling cycle, wherein liquid regenerant is now brought in from line 2 through line 39, through valve 211 and lines 38, 37, 36 and 35. The liquid then passes through valve 202 and lines 34 and 5 and flows up through adsorbent bed 101. As the first amount of liquid regenerant reaches the heated adsorbent bed 101, some of the regenerant vaporizes and provides some sensible cooling to the adsorbent bed. As the cooling process continues, the liquid regenerant is passed through the adsorbent bed 101 through line 6, line 11, valve 213, lines 12, 48 and 47 to valve 219. When adsorbent bed 102 is in this mode, the liquid regenerant is passed from adsorbent bed 102 through lines 15, 14, and 13 as controlled by valve 215 to join line 48. Similarly, when adsorbent bed 103 is in this mode, the liquid regenerant is passed from adsorbent bed 103 through lines 52, 50, and 49, as controlled by valve 217 to join line 48. From valve 219, the regenerant fluid flows along line 59 to line 60 where it passes through condenser 106. In condenser 106, initially the vaporized regenerant is condensed and sent via line 61 to tank 107. As the cooling process continues, the liquid regenerant having passed through adsorbent 101 travels the same path yet condenser 106 functions simply to produce a constant temperature for the collection of this material in tank 107. As with the condensed vapor regenerant during the heating process, the liquid regenerant collected during the cooling process is returned via line 63 from tank 107 through pump 108 and on line 64 to the separation section in the etherification zone for the recovery of the concentrated oxygenates. At the conclusion of the cooling step, the system again undergoes a displacement moving the current trim bed, adsorbent bed 103, to the lead position, adsorbent bed 101 to the trim position, and adsorbent bed 102 to the isolated regeneration steps. When adsorbent bed 102 is in the trim position, the ultra pure product is withdrawn from adsorbent bed 102 through lines 6 and 7, valve 212 and lines 8, 9 and 10.

In a typical application, the time required for a lead adsorption step or a trim adsorption step is 1440 minutes which is equivalent to a full regeneration cycle on a single adsorbent bed. The time required for all three beds to cycle through one complete sequence is 4320 minutes. The time for the pressure assisted drain step was 39 minutes, the heating step required 975 minutes, the cooling step required 420 minutes, and the displacement step required 6 minutes. The temperature of the superheated regeneration vapor ranged from 200°–300° C. The means for heating the regenerant material could range from a combination of low pressure and high pressure steam exchangers to a combination of steam exchangers and fired heaters or whatever means necessary to vaporize and superheat the regenerant to maintain the conditions necessary to desorb the oxygenates from the adsorbent undergoing regeneration.

The purified heavy hydrocarbon stream from the oxygenate recovery unit is further processed to increase its octane value. Downstream processes most commonly used are alkylation for making a high octane hydrocarbons for direct use as motor fuel components and dehydrogenation for producing additional isoalkene feed that is recycled to etherification zone. Suitable arrangements for alkylation and dehydrogenation are well known to those skilled in the art and require no additional explanation. An especially useful recycling combination of dehydrogenation, isomerization and etherification for the production of MTBE is shown in U.S. Pat. No. 4,816,607 and uses a deisobutanizer column to separate an isobutane overhead stream and a normal butane sidecut stream from a mixed $C_4$ feedstream, an isobutane recycle stream from the etherification zone and an isobutane effluent stream from an isomerization zone.

A broad range of catalysts are commercially available for the hydrogenation zone. Suitable catalyst for this process will completely saturate mono-and polyolefinic hydrocarbons without significant cracking or polymerization activity. Such catalysts will normally comprise one or more metallic components which may be elemental metal or a metal compound. The metals are normally chosen from Groups VIII and IVA of the Periodic Table of the elements with Ni, Pd, Pt, Sn, being common metals in these catalysts. Pt is a preferred metal in these catalysts. Based on the weight of the metal, the catalyst may contain from 0.1 to 4.0 wt. % metallic components. The metallic components of the catalyst are supported by a refractory inorganic oxide material such as one of the aluminas, silica, silica-alumina mixtures, various clays and natural or synthetic zeolitic materials. Preferably, the carrier material is alumina. Metallic components may be added to the carrier which is in the form of spheres, pellets or extrudates by impregnation, cogelation or coprecipitation. Preferably, the metallic components are impregnated by immersion of an extruded particle in an aqueous solution of a metal-containing compound and thereafter treating the impregnated particle by drying, calcination or other treatments.

Figure 2:
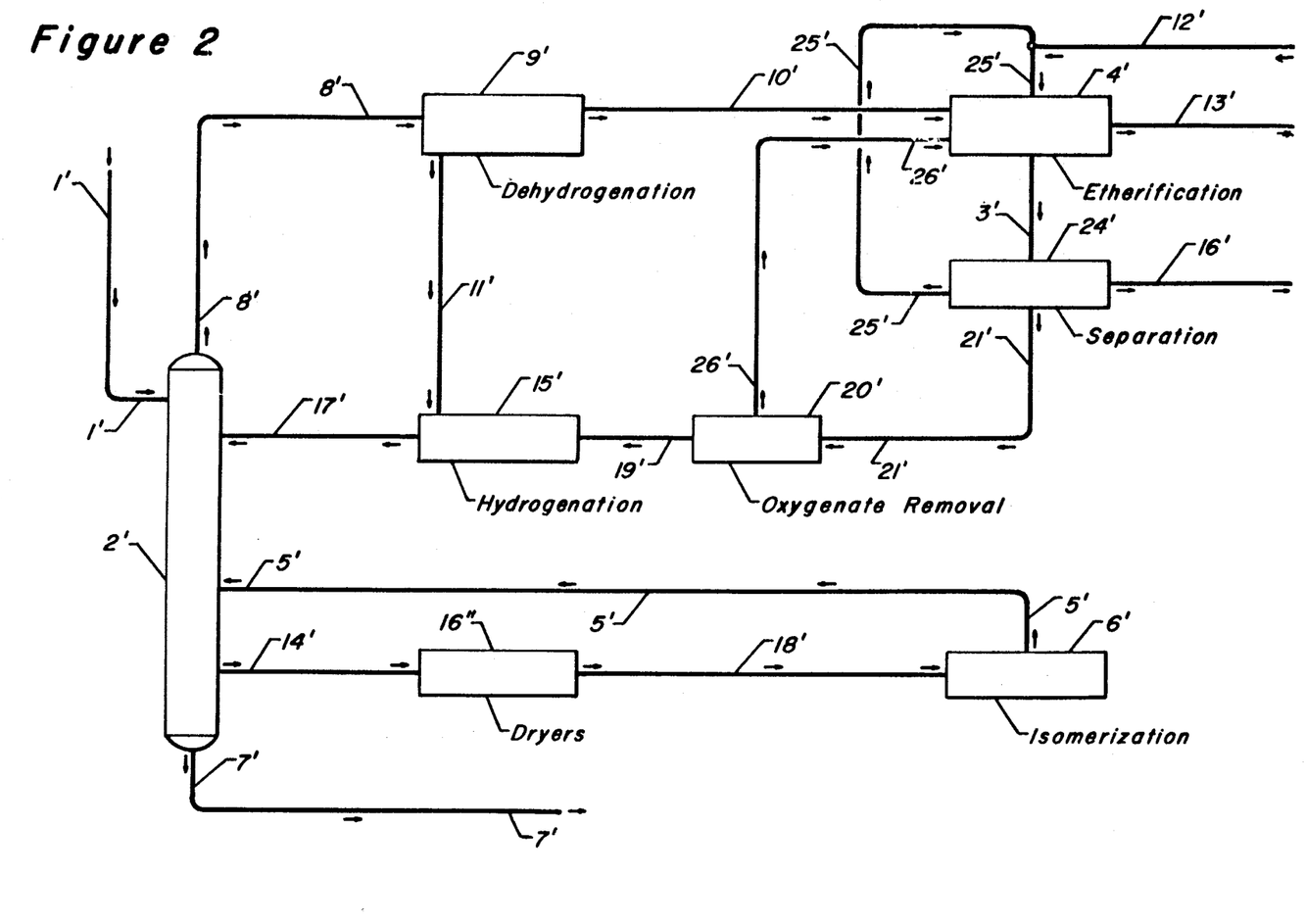
FIG. 2 schematically illustrates a combined dehydrogenation isomerization, and etherification process. This process includes a dehydrogenation reactor section 9', an isomerization section 6', an etherification reactor and first separation section 4', a methanol recovery unit 22', an oxygenate removal unit 21', and a hydrogenation section 15'.

In another aspect of the invention illustrated by the following process description made with reference to the flow diagram of FIG. 2 of the drawings: the instant invention is shown as a component of an integrated scheme for the production of methyl tertiary butyl ether from a mixture of butanes. The mixed butane feed comprising iso and normal butane are charged via line 1' to a deisobutanizer column 2' wherein the isobutane is taken overhead as stream 8' and passed to a dehydrogenation reaction and separation section 9', wherein hydrogen is collected, a portion of which is sent via line 11' to a hydrogenation step 15'. The output from the dehydrogenation section consisting largely of isoolefins of the $C_4$ range and $C_3$ and lighter hydrocarbons is sent via line 10' to an etherification section and first separation section 4' wherein the MTBE is produced by the reaction of isoolefin with a mole excess of methanol over a catalyst.

In the preferred etherification process for the production of MTBE, essentially all of the isobutene is converted to MTBE thereby eliminating the need for separating that olefin from isobutane. As a result, downstream separation facilities are simplified and operated more economically since these facilities need to handle a reduced volume of closely boiling materials. Several suitable etherification processes have been described in the available literature, with these processes being presently used to produce MTBE. The preferred form of the etherification zone is similar to that described in U.S. Pat. No. 4,219,678. In this instance, the isobutene containing stream 10', methanol feedstream 12' and a recycle stream 25' containing recovered excess alcohol are passed into the etherification zone 4' and contacted with an acidic etherification catalyst at etherification conditions.

A wide range of materials are known to be effective as etherification catalysts reactants including mineral acids such as sulfuric acid, boron trifluoride, phosphoric acid on kieselguhr, phosphorus-modified zeolites, heteropoly acids, and various sulfonated resins. The use of a sulfonated solid resin catalyst is preferred. These resin type catalysts include the reaction products of phenolformaldehyde resins and sulfuric acid and sulfonated polystyrene resins including those cross-linked with divinylbenzene. Further information on suitable etherification catalysts may be obtained by reference to U.S. Pat. Nos. 2,480,940, 2,922,822, and 4,270,929 and the previously cited etherification references.

A wide range of operating conditions are employed in processes for producing ethers from olefins and alcohols. Many of these include vapor, liquid or mixed phase operations. The etherification zones contains a sulfonated solid resin catalyst and operates at a temperature in the range of from 30°-100° C. (85°-212° F.) and a pressure of from 10 to 40 bars. Processes operating with vapor or mixed phase conditions may be suitably employed in this invention. The preferred etherification process uses liquid phase conditions. The reactor effluent of the etherification process is passed to a first separation zone wherein the MTBE product is withdrawn by line 13' and the unreacted isoalkanes as well as trace oxygenate by-products and unreacted methanol are recovered and passed via line 3' to the methanol recovery section and second separation section 24'. In the methanol recovery section, the unreacted methanol is removed and returned to the etherification section 4' as stream 25'.

After the recovery of methanol, the remainder of the etherification effluent enters a second separation zone which divides the material into a lower boiling stream 16' of hydrocarbons and light oxygenate compounds and a higher boiling stream 21' comprising heavy oxygenate compounds and $C_4$ or heavier hydrocarbons that are suitable for further processing. This higher boiling stream 21' now comprising isoalkanes and trace oxygenates are taken to an oxygenate removal section 20' wherein the ultra pure 3-bed oxygenate removal process is practiced. The oxygenate containing regenerant is returned to the first separation zone 4'.

The separation zone removes recovered oxygenate compounds from the regenerant stream and the process. Heavier oxygenate compounds leave the separation zone with the ether product. Some of these heavy oxygenate compounds are product ethers, the recovery of which increases the product yield. Most other non-product oxygenate compounds are acceptable in the product stream so that the product stream offers these oxygenates a convenient collection point. Any lighter oxygenate compounds that enters the first separation section with the regenerant are again carried overhead from the first separation zone and either recovered in alcohol recovery unit or carried overhead with the light overhead of the second separation zone. The oxygenate-containing regenerant stream can enter the second separation zone directly or indirectly. For example the spent regenerant stream can be passed with the etherification feed into the etherification zone and passed into the separation zone via line 26' as part of the etherification effluent. The ultra pure product, stream 19', is then sent to a hydrogenation section where any remaining diene or olefin bonds are saturated and a completely saturated product is sent via line 17' to the deisobutanizer 2'. A sidedraw, withdrawn as stream 14' and comprising normal alkanes, is sent through dryers 16' to line 18' and from line 18' to isomerization section 6'. The isomerization section contains a catalyst system which is deleteriously effected by both water and the presence of trace amounts of oxygenates. It is preferred that the oxygenates coming to section 6' be in concentrations ranging from 1 to 0.1 ppm wt. After isomerization over a platinum containing catalyst, the isomerized butane is returned via stream 5' to a point in the deisobutanizer above where the sidedraw stream 14' was taken. A stream of $C_5+$ hydrocarbons is withdrawn from the bottom of the deisobutanizer as stream 7'. This stream prevents the build-up of heavier hydrocarbons in the system.

What is claimed is:

1. A process for the liquid phase adsorption of oxygenates comprising light alcohols and ethers from a liquid hydrocarbon feedstock to produce an ultra pure product comprising:

(a) passing said liquid hydrocarbon feedstock to a first absorbent bed of two adsorbent beds simultaneously operating in a lead/trim configuration at adsorption conditions, each of said adsorbent beds having a feed end and an effluent end, and each of said adsorbent beds containing a solid adsorbent having a useful capacity and a selectivity for the adsorption of said oxygenates to establish a mass transfer zone in said first adsorbent bed, and withdrawing an intermediate stream from the effluent end of said first adsorbent bed;

(b) passing said intermediate stream to the feed end of a second adsorbent bed and withdrawing an ultra pure product having an oxygenate concentration of less than 1 ppm wt. from said second adsorbent bed;

(c) continuing steps (a) and (b) until the mass transfer zone has proceeded through said first adsorbent bed and is established in said second adsorbent bed at a point where the mass transfer zone has used less than about 10% of the useful capacity of said second adsorbent bed;

(d) terminating the passage of said hydrocarbon feedstock to said first adsorbent bed and passing said hydrocarbon feedstock to a third adsorbent bed that has undergone regeneration and contains a liquid regenerant in the void spaces of said solid adsorbent, displacing said liquid regenerant from the third adsorbent bed by passage of said feedstock therethrough to provide a displaced liquid regenerant and passing said displaced liquid regenerant to said first adsorbent bed, and passing an unadsorbed feedstock stream from said first adsorbent bed to said second adsorbent bed and recovering the ultra pure product from said second adsorbent bed for the duration of the displacement;

(e) terminating the passage of said hydrocarbon feedstock to said third adsorbent bed and passing said hydrocarbon feedstock to said second adsorbent bed to provide the intermediate stream, passing said intermediate stream to said third adsorbent bed and recovering the ultra pure product from said third adsorbent bed;

(f) terminating the flow of said displaced liquid regenerant to said first adsorbent bed and isolating said first adsorbent bed, draining said displaced liquid regenerant from said first adsorbent bed, passing a superheated regenerant vapor to said first adsorbent bed at a temperature effective to desorb oxygenates from the solid adsorbent, recovering said oxygenates from said first adsorbent bed in a spent regenerant vapor stream, and cooling said first adsorbent bed by passing said liquid regenerant to the feed end of said first adsorbent bed and recovering said liquid regenerant; and, (g) terminating the flow of the liquid regenerant to said first adsorbent bed and periodically incrementing the process cycle of steps (d)-(f) for said second adsorbent bed and said third adsorbent bed.

2. The process of claim 1 wherein the absorbent for the adsorbent beds in an activated alumina or a zeolitic molecular sieve.

3. The process of claim 1 wherein the adsorbent for the adsorbent beds is zeolite 13X.

4. The process of claim 1 wherein the adsorbent beds operate at adsorption conditions including a temperature of between 30° and 60° C.

5. The process of claim 1 wherein the temperature of the superheated regenerant is between 240° and 315° C.

6. The process of claim 1 wherein said regenerant is saturated ultra pure product.

7. The process of claim 1 wherein the ultra pure product contains between 1 and 0.1 ppm wt. oxygenates.

8. The process of claim 1, step (d) wherein the first adsorbent bed is drained by passing a portion of the superheated regenerant vapor stream to the effluent end of said first adsorbent bed to force the displaced liquid regenerant from said first adsorbent bed.

9. The process of claim 1 further comprising condensing the spent regenerant vapor stream to provide a hydrocarbon phase comprising regenerant and oxygenates and an aqueous phase comprising oxygenates and recovering said hydrocarbon phase and said aqueous phase.

10. A process for producing ethers comprising:

(a) passing an etherification feedstream comprising isoolefins and isoalkanes having four or five carbon atoms to an etherification zone;

(b) combining the etherification feedstream with a $C_1$-$C_5$ monohydroxy alcohol in said etherification zone at etherification conditions to obtain essentially complete conversion of said etherification feedstream and to provide an etherification zone effluent comprising isoalkanes, alcohol, ethers and light hydrocarbons;

(c) passing said etherification zone effluent to a first separation zone and recovering at least a first stream comprising an ether product and a second stream comprising isoalkanes, light hydrocarbons and oxygenate compounds including alcohol and ethers;

(d) recovering at least a portion of said alcohol from said second stream in an alcohol recovery zone to provide a recovered alcohol and returning at least a portion of the recovered alcohol to said etherification zone;

(e) passing the remainder of said second stream from said alcohol recovery zone to a second separation zone to separate isoalkanes from said second stream and obtain a third stream comprising isoalkanes and oxygenates;

(f) passing said third stream to an adsorption zone that uses separate beds containing a solid adsorbent having a useful capacity and a selectivity for the adsorption of oxygenates and simultaneously operating two of the beds in a lead/trim configuration at adsorption conditions, each of said adsorbent beds having a feed end and an effluent end, for the adsorption of oxygenates said adsorption zone operating by:

(i) passing said third stream to a first absorbent bed of two adsorbent beds to establish a mass transfer zone in said first adsorbent bed, and withdrawing an intermediate stream from the effluent end of said first adsorbent bed, passing said intermediate stream to the feed end of a second adsorbent bed and withdrawing an ultra pure product having an oxygenate concentration of less than 1 ppm wt. from said second adsorbent bed;

(ii) continuing step (i) until the mass transfer zone has proceeded through said first adsorbent bed and is established in said second adsorbent bed at a point where the mass transfer zone has used less than about 10% of the useful capacity of said second adsorbent bed;

(iii) terminating the passage of said third stream into said first adsorbent bed and passing said third stream to a third adsorbent bed that has undergone regeneration and contains a liquid regenerant in the void spaces of said solid adsorbent, displacing said liquid regenerant from the third adsorbent bed by passage of said third stream therethrough to provide a displaced liquid regenerant and passing the displaced liquid regenerant to said first adsorbent bed, and passing an unadsorbed feedstock stream from said first adsorbent bed to said second adsorbent bed and recovering the ultra pure product from said second adsorbent bed for the duration of the displacement;

(iv) terminating the passage of said third stream to said third adsorbent bed and passing said third stream to said second adsorbent bed, recovering the intermediate stream from said second adsorbent bed and passing said intermediate stream to said third adsorbent bed, and recovering the ultra pure product from said third adsorbent bed;

(v) terminating the flow of the displaced liquid regenerant to said first adsorbent bed and isolating said first adsorbent bed, draining said displaced liquid regenerant from said first adsorbent bed, passing a superheated regenerant vapor stream to said first adsorbent bed at a temperature effective to desorb oxygenates from the solid adsorbent and recovering said oxygenates from said first adsorbent bed in a spent regenerant vapor stream, and cooling said first adsorbent bed by passing said liquid regenerant to the feed end of said first adsorbent bed and recovering said liquid regenerant;

(vi) terminating the flow of the liquid regenerant to said first adsorbent bed and periodically incrementing the process cycle of steps (iii)–(v) for said second and third adsorbent beds; and, (g) passing said ultra pure product from said oxygenate recovery zone into said first separation zone.

11. The process of claim 10 wherein said etherification feedstream includes $C_4$ isoolefins, said monohydroxy alcohol of step (b) is methanol and said etherification zone produces MTBE.

12. The process of claim 10 wherein said etherification feedstream includes $C_4$ isoolefins, said monohydroxy alcohol of step (b) is ethanol and said etherification zone product is ETBE.

13. The process of claim 10 wherein said etherification feedstream is a dehydrogenation zone effluent stream that includes $C_1$–$C_3$ hydrocarbons and traces of hydrogen.

14. The process of claim 10 wherein said etherification contains a sulfonated solid resin catalyst and operates at a temperature in the range of from 30°–100° C. (85°–210° F.) and a pressure of from 10–40 bars.

15. The process of claim 10 wherein said regenerant is comprised of at least a portion of said ultra pure product.

16. The process of claim 10 step (f) wherein said solid adsorbent is activated alumina or a zeolitic molecular sieve.

17. The process of claim 10 step (f) wherein the adsorbent for the adsorbent beds is zeolite 13X.

18. The process of claim 10 step (f) wherein the adsorbent beds operate at an adsorption condition of between 30° and 60° C.

19. The process of claim 10 step (f) wherein the temperature of the superheated regenerant is between 240° and 315° C.

20. The process of claim 10 step (f) wherein the ultra pure product contains between 1 and 0.1 ppm wt. oxygenates.

21. The process of claim 10 step (f)(v) wherein the first adsorbent bed is drained by passing a portion of the superheated regenerant vapor stream to the effluent end of said first adsorbent bed to force displaced liquid regenerant from said first adsorbent bed.

22. The process of claim 10 step (f)(v) further comprising condensing the spent regenerant vapor stream to provide a hydrocarbon phase comprising regenerant and oxygenates and an aqueous phase comprising oxygenates recovering and said hydrocarbon phase and said aqueous phase.

* * * * *